United States Patent
Speelpenning et al.

(10) Patent No.: US 10,194,985 B2
(45) Date of Patent: Feb. 5, 2019

(54) SKIN TREATMENT APPARATUS WITH ADAPTIVE MOTION FEEDBACK

(71) Applicant: KONINKLIJKE PHILIPS N.V., Eindhoven (NL)

(72) Inventors: Tess Speelpenning, Eindhoven (NL); Henriette Christine Marie Hoonhout, Eindhoven (NL); Aleksey Anatolievich Kharin, Eindhoven (NL); Mart Kornelis-Jan Te Velde, Eindhvoen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 114 days.

(21) Appl. No.: 14/890,703

(22) PCT Filed: May 23, 2014

(86) PCT No.: PCT/EP2014/060592
§ 371 (c)(1),
(2) Date: Nov. 12, 2015

(87) PCT Pub. No.: WO2014/187927
PCT Pub. Date: Nov. 27, 2014

(65) Prior Publication Data
US 2016/0106505 A1    Apr. 21, 2016

(30) Foreign Application Priority Data

May 23, 2013    (EP) ..................................... 13168841

(51) Int. Cl.
*A61B 18/20*    (2006.01)
*A61N 5/06*    (2006.01)
(Continued)

(52) U.S. Cl.
CPC ............ *A61B 18/203* (2013.01); *A61B 5/441* (2013.01); *A61N 5/0616* (2013.01);
(Continued)

(58) Field of Classification Search
CPC .... A61N 2005/0654; A61B 2560/0475; A61B 2018/202; A61B 2018/0091;
(Continued)

(56) References Cited

U.S. PATENT DOCUMENTS 7,204,832 B2    4/2007    Altshuler
8,361,775 B2    1/2013    Flower
(Continued)

FOREIGN PATENT DOCUMENTS

WO    2012106678 A1    8/2012

*Primary Examiner* — Gary Jackson
*Assistant Examiner* — Youwon Kahng (57) ABSTRACT

A skin treatment device (100) comprises: —a housing (101); —a treatment action performer (110) arranged within the housing (101) for performing a treatment action on the user's skin (2); —a speed sensor (120) for sensing a relative speed between the housing and the user's skin; —a speed feedback signalling device (400); —a control device (140) receiving an output signal from the speed sensor. The control device controls the speed feedback signalling device if the output signal received from the speed sensor is outside a tolerated displacement speed range (R). The tolerated displacement speed range is adapted to the skills of the user to move the device over the skin surface with a constant speed. If the user's skills are relatively low, the control device increases the magnitude of the tolerated displacement speed range.

14 Claims, 7 Drawing Sheets

(51) Int. Cl.
- *A61B 5/00* (2006.01)
- *A61B 18/00* (2006.01)
- *A61B 17/00* (2006.01)

(52) U.S. Cl.
CPC ............... *A61B 2017/00075* (2013.01); *A61B 2017/00128* (2013.01); *A61B 2017/00132* (2013.01); *A61B 2018/0091* (2013.01); *A61B 2018/00476* (2013.01); *A61B 2018/00642* (2013.01); *A61B 2018/00904* (2013.01); *A61B 2018/202* (2013.01); *A61B 2560/0475* (2013.01); *A61N 2005/0644* (2013.01); *A61N 2005/0654* (2013.01)

(58) Field of Classification Search
CPC ........... A61B 2018/00904; A61B 2018/00642; A61B 2018/00476; A61B 2017/00132; A61B 2017/00128; A61B 2017/00075; A61B 18/203; A61B 5/441
See application file for complete search history.

(56) References Cited

U.S. PATENT DOCUMENTS

| | | |
|---|---|---|
| 2007/0129771 A1 | 6/2007 | Ku Rtz |
| 2011/0166559 A1 | 7/2011 | Eckhouse |
| 2011/0245735 A1 | 10/2011 | Eckhouse |
| 2012/0022510 A1 | 1/2012 | Welches |
| 2012/0197357 A1 | 8/2012 | Dewey |
| 2012/0283710 A1 | 11/2012 | Liu |
| 2012/0283803 A1* | 11/2012 | Liu ..................... A61B 18/203 607/89 |
| 2016/0058509 A1* | 3/2016 | Van De Wouw .... A61B 18/203 606/9 |

* cited by examiner

SKIN TREATMENT APPARATUS WITH ADAPTIVE MOTION FEEDBACK

This application is the U.S. National Phase application under 35 U.S.C. § 371 of International Application No. PCT/EP2014/060592, filed on May 23, 2014, which claims the benefit of European Application No. 13168841.8 filed on May 23, 2013. These applications are hereby incorporated by reference herein.

FIELD OF THE INVENTION

The present invention relates in general to skin treatment apparatus of the type comprising a treatment device that is to be moved over the skin surface manually. In this context, the term "treatment" is used in the broadest sense. The treatment may involve for instance skin care and/or skin rejuvenation, or for instance removal of hair such as epilation or depilation. The treatment may be purely for cosmetic reasons. In a possible embodiment, the treatment apparatus is an epilation apparatus, for example a light-based epilation apparatus or photo epilator, and the present invention will be explained in more detail for this type of devices.

BACKGROUND OF THE INVENTION

In skin treatment, generally speaking, a skin treatment device contains an active treatment component that acts on the skin. This component, in operation, performs a treatment action on the skin that constitutes the actual treatment. The action may be mechanical, such as for instance in the case of shaving devices, depilation devices, mechanical epilation devices, cleaning devices, skin rejuvenation devices, etc. The action may be thermal, such as for instance in the case of optical depilation devices where a light beam is applied to the skin in order to affect part of the hair follicles. The action may be optical. In the case of optical depilation devices, the prior art comprises flash-type embodiments that generate one light flash or a limited number of flashes, and the user is supposed to hold the device steady during flashing and to displace the device in between flashes. The present invention, by contrast, relates to continuously operating devices that need to be moved over the skin surface continuously. It is noted in this respect that "continuously operating" includes the situation where a device is continuously generating light flashes, so that the device has to be displaced while performing the treatment.

In most, if not all, cases where the device has to be moved over the skin whilst in operation, optimum results require an optimum displacement speed. It will easily be understood that the treatment may be less effective if the displacement speed is too high, but the treatment may also be less effective if the displacement speed is too low, or worse, damage could be done to the user's skin if the device is displaced too slowly or, even worse, is held still.

It is true that the user manual may inform the user of the optimum speed or optimum speed range, but a problem for the users is how they should determine that they are actually moving the device at the right speed. In practice, this means that users have to go through a lengthy learning process before they have developed a "feeling" for the correct speed and are able to apply the correct speed consistently.

To assist the user in this learning process, solutions have already been proposed, according to which the device is provided with a speed sensor for detecting the relative speed between the device and the skin, and wherein the device is provided with an indicator giving the user feedback information. If the user is moving the device at a correct speed, information of a first type (or no information) is given to the user, but if the user is moving the device either too fast or too slow, information of a second type is given to the user, which will allow the user to adapt the speed and move slower or faster, respectively. For assisting the user in this way, the type of feedback signal is not essential.

For instance, the feedback signal may be a sound signal, or a tactile signal, such as vibrations, or an optical signal. US-2007/0129771 discloses a device where the indicator gives an optical signal.

However, it has been found to be very difficult for the user to handle the device at the correct speed. A feedback system may help by informing the user that the current speed is out of range, and although such a feedback system may be very simple, it appears to be very difficult for the user to move the device at the correct speed. Especially when the device is new to the user, the effect of the feedback signals may be less than expected a priori. The user will go too fast or too slow many times, and will hence receive many feedback signals pointing out these mistakes. With time and practice, the user's performance will improve, and the amount of "error signals" will decrease, but the user needs to be patient. However, it is quite possible that a user gets frustrated by receiving so many "error signals" and by not experiencing improvement quickly enough, which causes the user to give up and stop using the device altogether.

SUMMARY OF THE INVENTION

A general object of the present invention is to overcome the above-mentioned problem. More particularly, the present invention aims to provide an improved skin treatment device that assists its user in improving his/her performance with a reduced risk of frustrating an impatient user.

According to the present invention, this general object is achieved by adapting threshold levels of the displacement speed feedback to the performance skills of the user. More particularly, in order to achieve the above object, the present invention provides a skin treatment device comprising:

a housing whose shape and size are suitable for being held by a human hand;

a treatment action performer associated with the housing for performing a treatment action on a user's skin;

a speed sensor for sensing a relative displacement speed between the housing and the user's skin in a device displacement direction parallel to a surface of the skin;

a speed feedback signalling device comprising a signal generator for generating a signal perceivable by a human;

a control device provided with an associated memory containing information defining a tolerated displacement speed range, the tolerated displacement speed range having an upper threshold and a lower threshold;

wherein the control device is coupled to receive an output signal from the speed sensor and is coupled to provide a control signal to the speed feedback signalling device;

wherein the control device is adapted to compare the speed sensor output signal with said upper threshold and with said lower threshold, and to control the speed feedback signalling device such as to generate a first feedback signal when the speed sensor output signal indicates that the relative displacement speed is higher than said upper threshold and to generate a second feedback signal when the speed sensor output signal indicates that the relative displacement speed is lower than said lower threshold;

wherein the control device is adapted to monitor a parameter indicative of a degree of a user's skill to operate the skin treatment device;
wherein the control device is adapted to set a relatively large magnitude of, or increase the magnitude of, the tolerated displacement speed range if said parameter indicates a relatively low degree of said user's skill;
and wherein the control device is adapted to set a relatively small magnitude of, or decrease, the magnitude of, the tolerated displacement speed range if said parameter indicates a relatively high degree of said user's skill.

In a particular embodiment, the skin treatment device has a target operational range of the relative displacement speed, with a target operational upper limit and a target operational lower limit, wherein the control device is adapted to calculate the upper threshold according to the formula V1=OV1+TM1 and to calculate the lower threshold according to the formula V2=OV2−TM2, in which:

V1 indicates the value of the upper threshold,
V2 indicates the value of the lower threshold,
OV1 indicates the value of the target operational upper limit,
OV2 indicates the value of the target operational lower limit,
TM1 indicates an upper tolerance margin,
TM2 indicates a lower tolerance margin;

and wherein the control device is adapted to increase at least one of said upper and lower tolerance margins for less skilled users and to decrease at least one of said upper and lower tolerance margins for more skilled users.

For increased clarity of the feedback, the first feedback signal and the second feedback signal may be mutually different.

In a preferred embodiment of the skin treatment device according to the invention, the control device is adapted to analyse the speed sensor output signal and to rate the parameter indicative of the degree of said user's skill in real time on the basis of the outcome of this analysis. In a practical embodiment, the control device is adapted to analyse the speed sensor output signal by obtaining and analysing a frequency profile of the speed sensor output signal. In a simple embodiment, the control device is adapted to analyse the speed sensor output signal by measuring and analysing an amplitude of the speed sensor output signal at a certain frequency or within a certain frequency band or above a certain cut-off frequency.

In a possible embodiment, the control device is adapted to monitor a number of times and/or an amount of time that the device has actually been used, and to decrease the magnitude of the tolerated displacement speed range as the number of times the device has actually been used increases and/or the amount of time the device has actually been used increases, respectively.

In order to reduce a "run-in" time when the device is used again a next time, it is preferred that the control device is adapted to store, in the memory, data defining the magnitude of the tolerated displacement speed range, or adapted to store, in the memory, data defining the target operational range, or adapted to store, in the memory, data defining the values of the upper and lower tolerance margins.

In a particularly advantageous embodiment, the control device is capable of adapting the target operational range. The device may advantageously be provided with a skin-type sensor for determining a skin type of the user's skin, to enable the control device to automatically adapt the target operational range to the skin type determined by the skin-type sensor.

In order to reduce the risk of possible harm to the user's skin, it is preferred that the control device is adapted to adapt a power level of the treatment action performer in conjunction with an adaptation of the magnitude of the tolerated displacement speed range, wherein an increase of the magnitude of the tolerated displacement speed range is associated with a reduction of the power level.

Further advantageous elaborations of the skin treatment device according to the invention are mentioned in the dependent claims and are discussed in the below detailed description of the invention.

BRIEF DESCRIPTION OF THE DRAWINGS

These and other aspects, features and advantages of the present invention will be further explained by means of the following description of one or more preferred embodiments with reference to the drawings, in which same reference numerals indicate same or similar parts, and in which.

DETAILED DESCRIPTION OF THE INVENTION

Figure 1A:
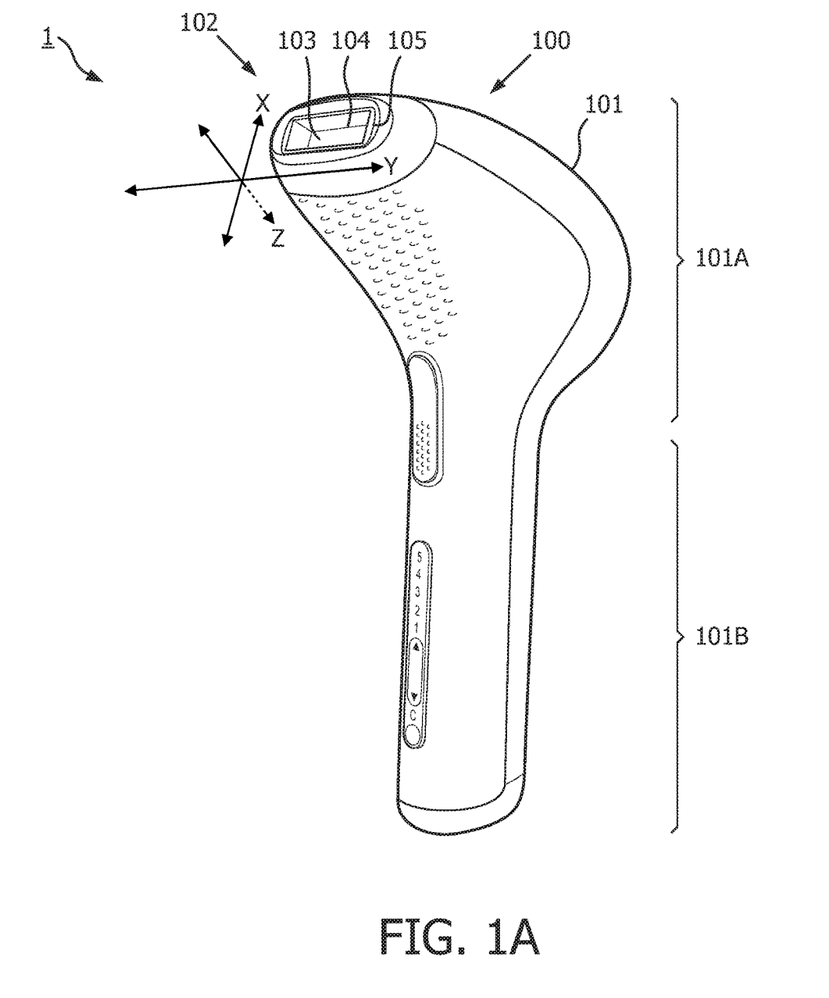
FIG. 1A schematically shows a perspective view of an example of a possible embodiment of a handheld skin treatment device according to the invention.
Figure 1B:
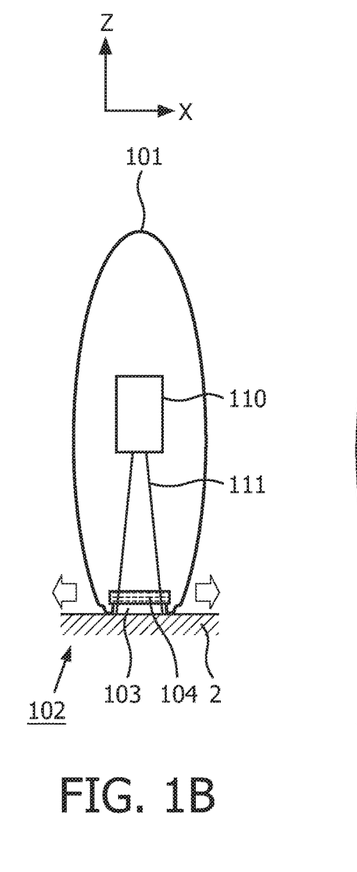
FIGS. 1B and 1C are schematic vertical cross sections of the handheld skin treatment device of FIG. 1A in mutually perpendicular directions.
Figure 1C:
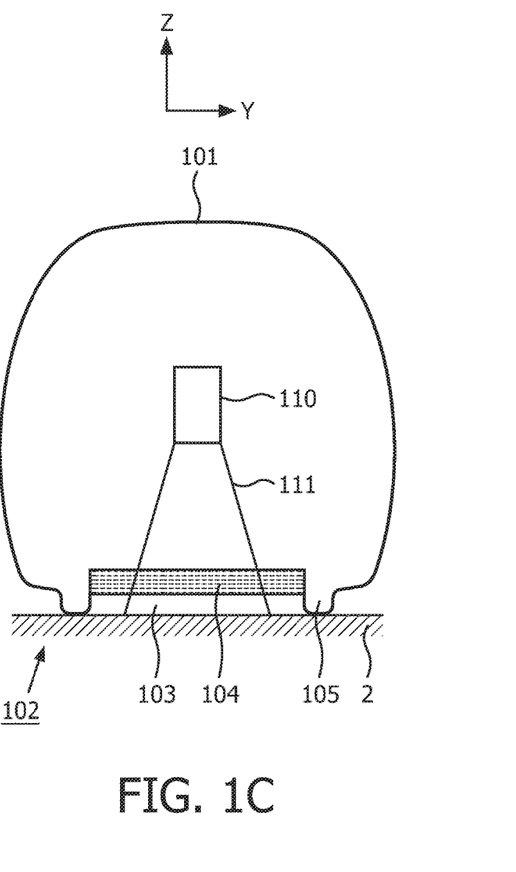

FIG. 1A shows a perspective view of a possible embodiment of a handheld skin treatment device 100, which is part of a skin treatment apparatus generally indicated by reference numeral 1. The skin treatment device 100 has a housing 101. The shape of the housing may be subject to design variations, but in this case the housing has a treatment portion 101A and a grip portion 101B of a size suitable for being held in human hands. In a top view, the housing 101 may have an elongate profile, which is practical but not essential. FIGS. 1B and 1C are schematic cross sections of the treatment portion 101A of the handheld device 100 in mutually perpendicular directions.

In use, the skin treatment device 100 is to be placed on the skin 2 of a user. The side of the housing 101 to be directed to the skin will be indicated as skin-side 102. In FIGS. 1B-1C this is the underside. Usually, the skin-side 102 of the housing is to be placed on the skin, i.e. actually contacts the skin, although it is possible that contactless devices are used.

In use, the skin treatment device 100 is to be moved over the skin of a user. It is possible that the skin treatment device 100 may be moved in any direction parallel to the skin, but in the context of the present explanation it will be assumed that the skin treatment device 100 has an intended movement direction. This intended movement direction will be indicated as X-direction. In the case of the housing 101 having an elongate profile, the X-direction may typically coincide with the smaller dimension of the housing 101, i.e. the width. The direction parallel to the skin and perpendicular to the X-direction will be indicated as Y-direction, typically coinciding with the longitudinal dimension of the housing 101, i.e. the length. The direction perpendicular to the skin will be indicated as Z-direction, typically coinciding with the height of the housing 101.

FIG. 1B is a cross section according to an XZ-plane, and FIG. 1C is a cross section according to a YZ-plane. The figures illustrate that the housing 101 accommodates an active component indicated as treatment action performer 110. The nature of the treatment action performer 110 depends on the nature of the skin treatment apparatus. The treatment may be mechanical, requiring mechanical contact between the treatment action performer 110 and the skin. In the illustrated example, the treatment is optical and the treatment action performer 110 comprises a device for illuminating the skin 2, for instance by scanning an optical beam 111 over the skin, or by producing light flashes, or by producing constant illumination. The treatment action performer 110 may itself comprise a light source, but it is also possible that the skin treatment apparatus 1 further includes an external light source (not shown for sake of simplicity), as well as an optical guidance system (for instance based on optical fibres) for transferring the light to the skin treatment device 100. In an example, the treatment caused by the optical beam 111 is removing hair by affecting hair follicles, and the present invention specifically, but not exclusively, relates to a hair removal device.

The treatment action performer 110 may be disposed outside the housing 101, or may have a portion extending through the housing. The treatment action performer 110 may be disposed entirely within the housing 101, in which case the skin-side 102 of the housing 101 has an opening 103 through which the treatment action performer 110 can act on the user's skin 2. In the case of an optical action, the opening 103 may be provided with a transparent cover 104 that is substantially transparent to the treatment light 111 but protects the interior of the housing 101 against moisture and dirt. The opening 103 will hereinafter also be indicated as "output window". It is noted that it is not essential that the cover 104 contacts the skin. In cases where the cover 104 tends to become hot, the cover 104 may lie recessed within a surrounding foot portion 105 of the housing 101.

The handheld device as described so far is known in practice.

The skin treatment device 100 is to be moved over the user's skin while the treatment action performer 110 is performing the treatment. It should be clear that it is important that the skin treatment device 100 is moved over the skin at a correct speed.

This is especially clear in the case of an optical epilation device. The treatment action performer 110 generates light containing a certain amount of energy per unit time, which is distributed over a surface area of the skin 2 corresponding to the size of the output window 103. Taking into account the displacement speed, this corresponds to a certain energy input per square centimeter of skin. If the skin treatment device 100 is displaced too fast, the treatment is inadequate. If the skin treatment device 100 is displaced too slowly, the skin receives too much energy and may be damaged. If the treatment is performed very slowly, this will lead to user dissatisfaction. Thus, the displacement speed should be a correct speed, or should be within a predetermined range of correct speeds. As indicated before, it is very difficult for a user to move the device with a precise and constant speed, and therefore to keep the speed within the limits of such a range.

According to a first aspect of the present invention, the skin treatment device 100 is provided with a speed sensor 120 for sensing the relative speed between the housing 101 and the skin 2.

Figure 2:
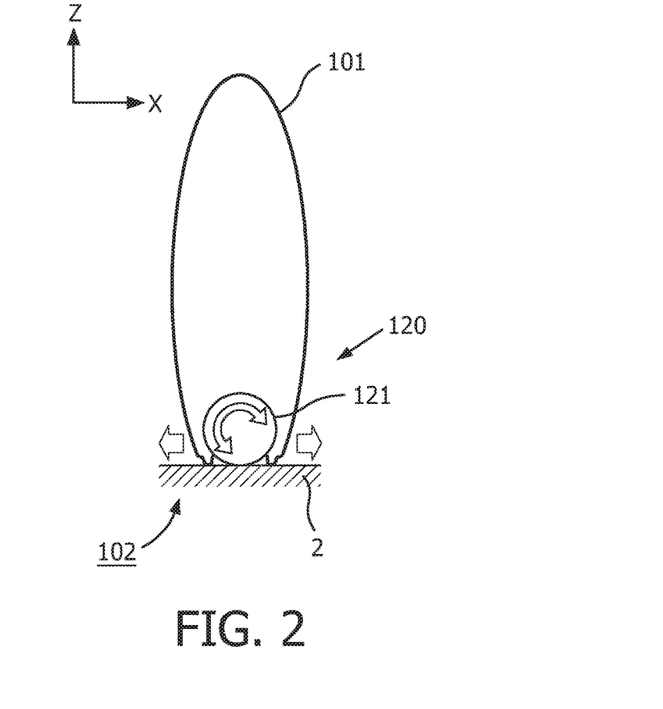
FIG. 2 is a schematic vertical cross section of a handheld skin treatment device.

FIG. 2 is a schematic cross section comparable to FIG. 1B, showing the speed sensor 120. For sake of convenience, the treatment action performer 110 is not shown in this figure. The speed sensor 120 may be any type of sensor, adapted to generate an output signal indicative of, or even proportional to, the said relative displacement speed. In a possible embodiment, the speed sensor 120 comprises a wheel 121, which touches the skin and which is rotated when the housing 101 is displaced in the X direction. Contact-free speed sensors are however also possible. In a possible embodiment, the speed sensor 120 comprises an LED for generating a detection beam towards the skin, and an optical detector for detecting reflected light. Speed sensors of this type are known per se, and are for instance used in computer mice. Such known sensors can be used in the skin treatment device 100 of the present invention. Therefore a more elaborate explanation of the design and operation of the speed sensor is not necessary. It is noted that the LED sensors as used in computer mice are also capable of detecting the relative direction of the displacement, i.e. an angle in the range between 0° and 360° in a virtual plane parallel to the skin.

Figure 3:
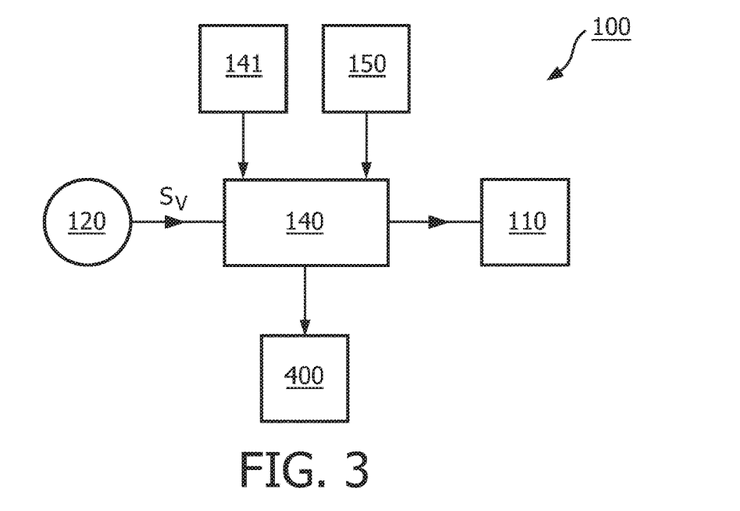
FIG. 3 is a schematic block diagram of a skin treatment device according to the invention.

FIG. 3 is a schematic block diagram, showing that the skin treatment device 100 also comprises a control device 140, for instance a suitably programmed microprocessor or controller or the like. The control device 140 has an associated memory 141 containing information defining an optimum speed or an optimum speed range. The control device 140 is coupled to receive an output signal from the speed sensor 120, and is arranged for controlling the treatment action performer 110. It may be possible that, within limits, the control device 140 can reduce the output power of the treatment action performer 110 if the speed is too low, or can increase the output power of the treatment action performer 110 if the speed is too high. However, in general, efficient treatment (e.g. hair removal) requires the treatment action performer 110 to be operated at its nominal output power, so that the regulating margin to higher output powers is small. Further, reducing the output power of the treatment action performer 110 at least results in increased treatment time, which in general is undesirable. Best results are achieved if the output power of the treatment action performer 110 is kept close to nominal and the displacement speed is kept close to optimal.

The skin treatment device 100 further comprises a speed feedback signalling device 400, controlled by the control device 140, as will be discussed below with reference to FIG. 4. The signalling device 400 comprises a signal generator, not shown for sake of simplicity, capable of generating the actual signal perceived by the user. If the signal is optical, the signal generator may comprise one or more LEDs or any other type of light source. If the signal is audible, the signal generator may comprise one or more beepers or any other type of sound source. If the signal is tactile, the signal generator may comprise one or more vibrators or any other type of mechanical signal generator. Combinations of the mentioned types of signal generators are also possible.

Figure 4:
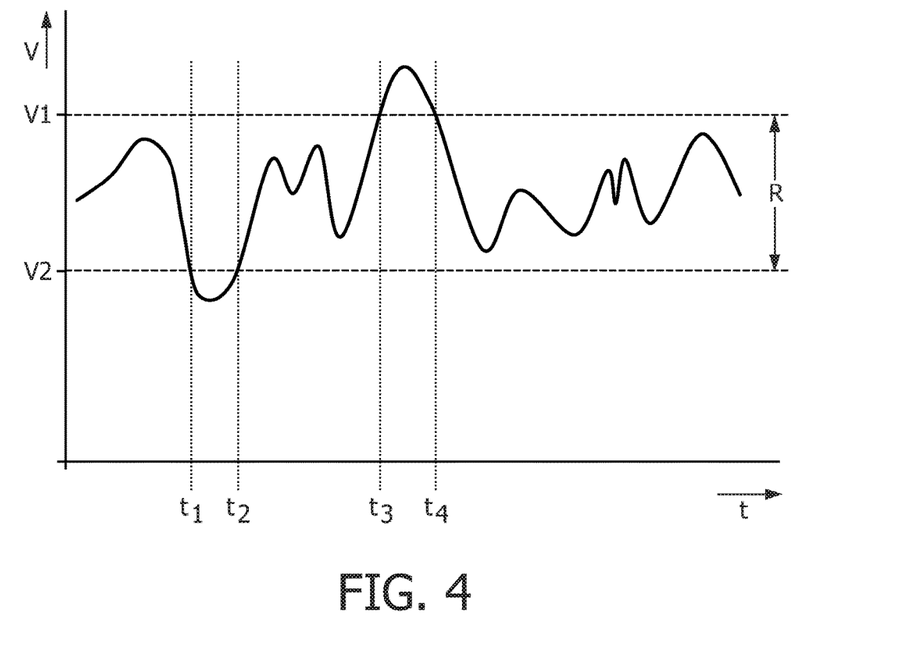
FIG. 4 is a graph for explaining the feedback signalling in a handheld skin treatment device according to the invention.

FIG. 4 is a graph, in which the horizontal axis represents time t in arbitrary units, and in which the vertical axis represents relative displacement speed V between the skin 2 and the device 100 or the housing 101, as measured by the sensor 120. V1 and V2 indicate two threshold levels, which between them define a range R of acceptable speeds. V1 indicates the upper limit of this speed range R, and will be indicated as "upper threshold". V2 indicates the lower limit of this speed range R, and will be indicated as "lower threshold". The control device 140 compares the actual speed V as measured by the sensor 120 (i.e. as represented by a sensor output signal $S_V$) with the upper and lower thresholds V1 and V2. If the momentary value of the sensor output signal $S_V$ indicates that the momentary displacement speed V is higher than the upper threshold V1, as happens between times t3 and t4 in FIG. 4, the control device 140 generates a control signal for the signalling device 400 to cause the signalling device 400 to generate a first feedback signal for the user to warn the user that the device is being moved too fast. If the momentary value of the sensor output signal $S_V$ indicates that the momentary displacement speed V is lower than the lower threshold V2, as happens between times t1 and t2 in FIG. 4, the control device 140 generates a control signal for the signalling device 400 to cause the signalling device 400 to generate a second feedback signal for the user to warn the user that the device is being moved too slowly. For increased clarity, these two feedback signals may be mutually different; for instance, in the case of sound signals, these two feedback signals may have a mutually different pitch.

Thus, as long as the actual displacement speed V is within this speed range R, no feedback signal is generated. Therefore, this range will briefly be indicated as "tolerated" speed range.

When the user does not perceive any feedback signal, he knows that the skin treatment device 100 is being moved at an acceptable speed. When the user perceives the first feedback signal, he knows that the speed should be decreased, and when the user perceives the second feedback signal, he knows that the speed should be increased.

In FIG. 4, the thresholds V1 and V2 are shown as being constant in time. However, it is a key feature of the present invention that the thresholds V1 and V2 are adaptable by the control device 140. The control device adapts these thresholds V1 and V2 on the basis of the performance skills of the user. To this end, the control device 140 is adapted to analyse the sensor output signal $S_V$ received from sensor 120.

Figure 5A:
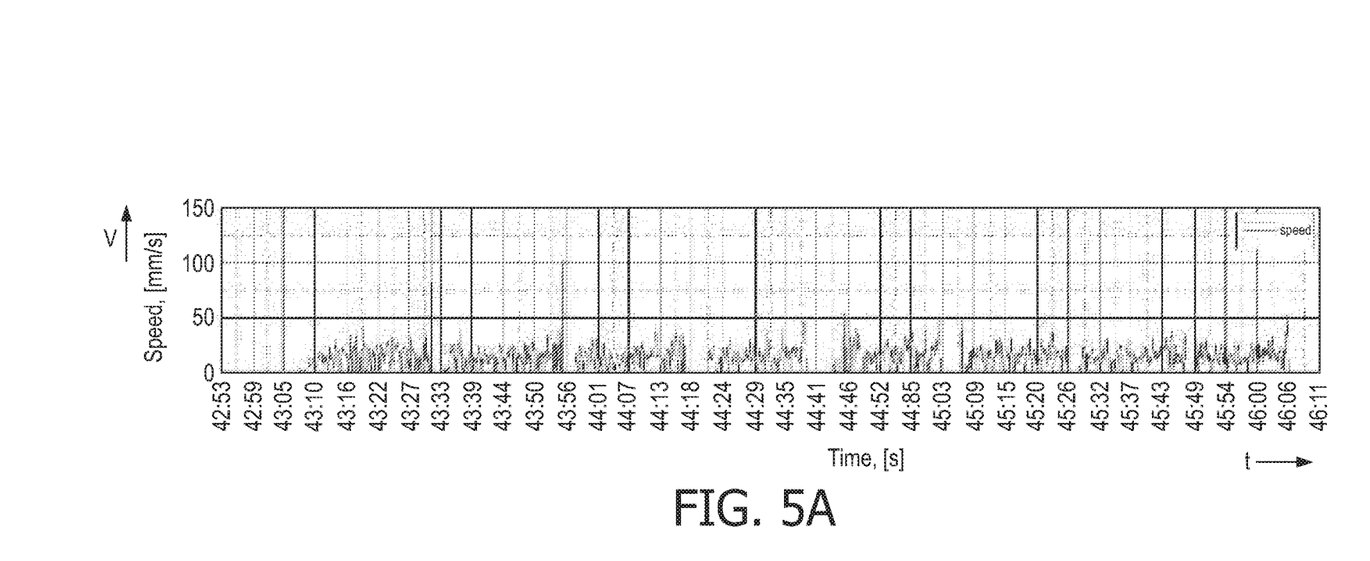
FIGS. 5A and 5B are graphs showing measured speed signals of an inexperienced user and an experienced user, respectively, using the skin treatment device according to the invention.
Figure 5B:
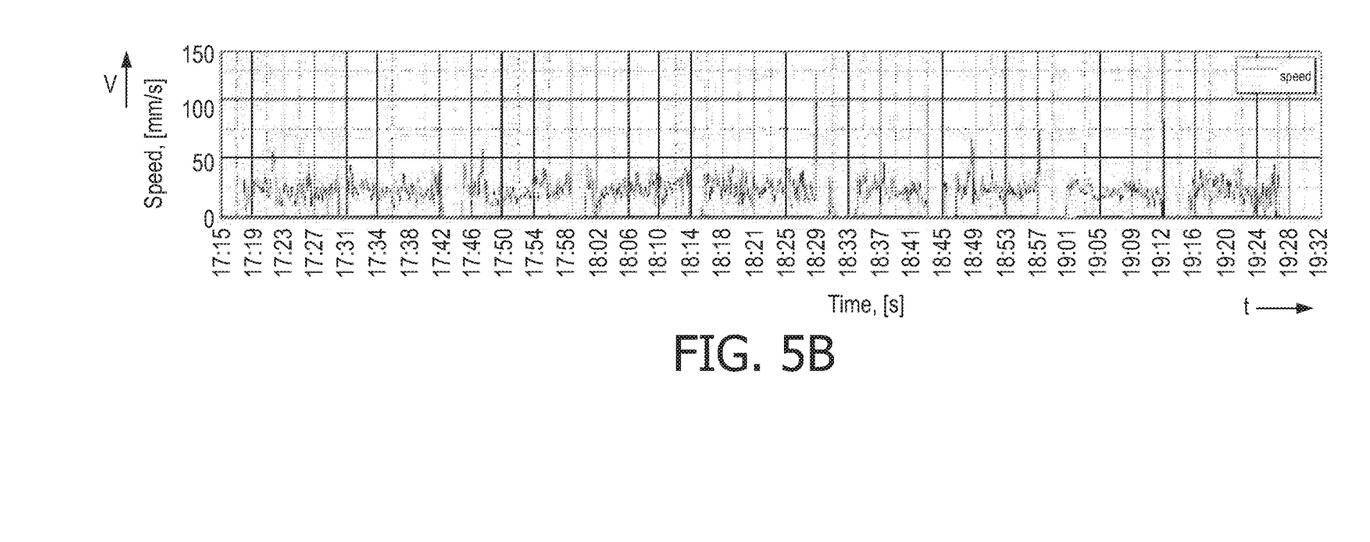

FIGS. 5A and 5B are graphs showing plots of displacement speed V (vertical axis) versus time (horizontal axis) as actually measured in a usability test. FIG. 5A shows the results of an inexperienced user, while FIG. 5B shows the results of a more experienced user. In both cases, the intended speed (target speed) was 30 mm/sec, and the graph shows multiple successive runs.

It can clearly be seen that the experienced user (FIG. 5B) has a more steady hand than the inexperienced user (FIG. 5A): the plot of the inexperienced user shows more speed fluctuations, and the fluctuations have higher amplitude.

Figure 6A:
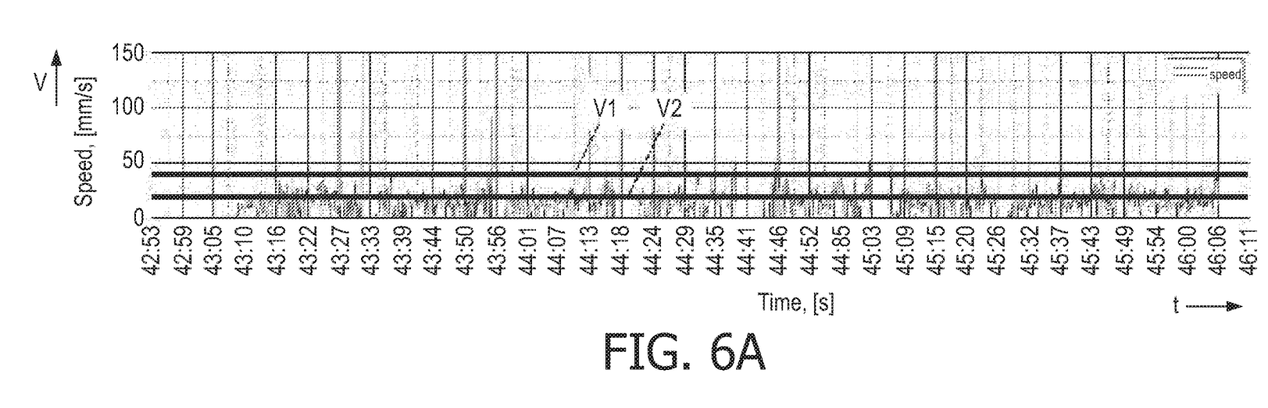
FIGS. 6A and 6B are graphs comparable to FIGS. 5A and 5B, respectively, including exemplary speed threshold lines.
Figure 6B:
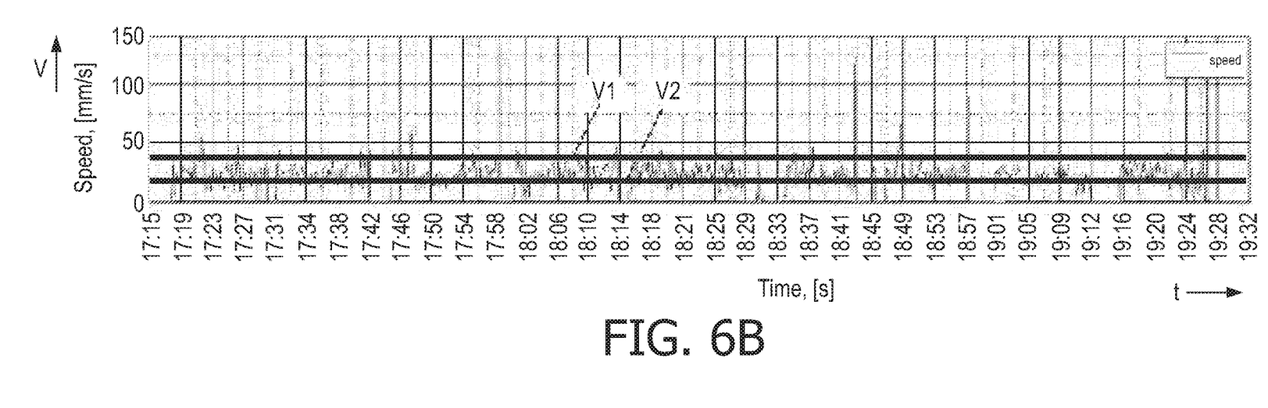

FIGS. 6A and 6B show the same plots, and additionally show exemplary threshold lines V1 and V2 for the sake of explanatory discussion. Assuming an upper threshold V1 at 40 mm/sec and a lower threshold V2 at 20 mm/sec, it can be seen that the experienced user would receive only a few corrective feedback signals, while the inexperienced user would receive corrective feedback signals almost continuously. This may be frustrating for the inexperienced user, to the extent that he/she might stop using the device and therefore never will become an experienced user. In addition, he/she will be dissatisfied with the device.

Figure 7A:
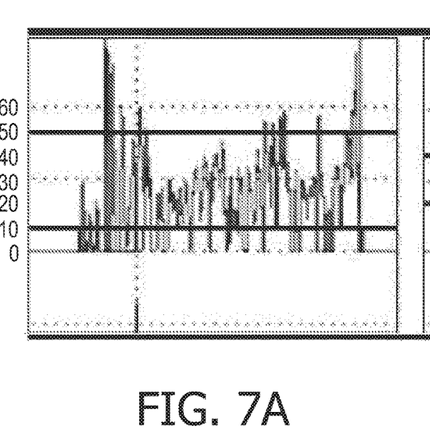
FIGS. 7A and 7B are graphs comparable to FIGS. 5A and 5B, respectively, including exemplary speed threshold lines.
Figure 7B:
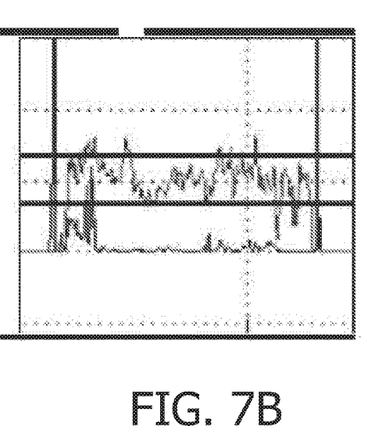

FIGS. 7A and 7B again show the same plots, again showing exemplary threshold lines V1 and V2 for the sake of explanatory discussion, but now the tolerated speed range for the inexperienced user is wider than the tolerated speed range for the experienced user. Assuming again an upper threshold V1 at 40 mm/sec and a lower threshold V2 at 20 mm/sec for the experienced user, but an upper threshold V1 at 50 mm/sec and a lower threshold V2 at 10 mm/sec for the inexperienced user, it can clearly be seen that the inexperienced user would now receive fewer corrective feedback signals. This is less frustrating for the inexperienced user, and he is more likely to persevere and become an experienced user.

In the following explanation, it will be assumed that a specific operational range OR of speeds associated with the device is defined. This operational range OR defines a range of speeds at which the best operational results are to be expected, and, ideally, the device is intended to be operated at an actual displacement speed V being within this operational range OR. Therefore, this range will briefly be indicated as "target" speed range. The target operational range OR will have a target operational upper limit OV1 and a target operational lower limit OV2. In principle, it is possible that OV1=OV2.

Data defining this target operational range OR may be stored in the memory 141.

The target operational range OR may be a fixed range, and may actually have been defined in advance by the manufacturer.

It is also possible that the target operational range OR is adaptable. As an example, the target operational range OR could be adapted to the skin type of the user.

Adaptation could be done by the user himself, and for this purpose the device may comprise a user interface of any suitable type, allowing user input to the control device 140. The adapted target operational range OR could be in the memory 141. It is also possible to have a skin-type user interface of which the momentary setting acts as a momentary definition for the target operational range OR, which may be particularly useful in cases where the device is intended to be used y multiple users.

Adaptation could alternatively be done by the control device 140 automatically. For this purpose, the device could be provided with a skin sensor 150, for instance an optical sensor detecting the colour of the skin.

It should be clear that the possible adaptations of the target speed range still serve the purpose of defining an objectively optimum range of displacement speeds, and are totally independent of defining a tolerated speed range to allow for a low level of user skills. As far as adapting the tolerated speed range is concerned, the target speed range serves as a basis. For calculating the tolerated speed range, the control device 140 is adapted to calculate an upper tolerance margin TM1 and a lower tolerance margin TM2, and to calculate the upper threshold V1 according to V1=OV1+TM1 and to calculate the lower threshold V2 according to V2=OV2−TM2. TM1 and TM2 are positive values, and may be equal to each other or may be mutually different.

For setting the tolerated speed range R, which in the above example corresponds to setting the tolerance margins TM1 and TM2, the control device 140 is adapted to monitor a parameter indicative of the user's operational skills, i.e. the user's ability to move the device at the correct speed. If said parameter indicates that the user has low operational skills, the control device 140 sets higher tolerance margins or increases the tolerance margins. Conversely, if said parameter indicates that the user has sufficient or good operational skills, the control device 140 sets lower tolerance margins or decreases the tolerance margins, and eventually the tolerance margins may even be zero.

In general, it may be assumed that the user's operational skills will improve with experience: the more the user actually uses the device, the more he will get used to maintaining a certain speed. The user will "learn". Based on this assumption, the present invention provides a simple embodiment in which the parameter monitored by the control device 140 is the number of times and/or the amount of time the user has actually used the device already. However, if it should be possible that the device is used by more than one user, this would require the use of user-specific memories, and an input member for allowing the user to indicate which user is going to use the device.

Likewise, it is possible for the control device 140 to monitor progress of the user. For a first-time, inexperienced user, the learning effect will be highest in the first couple of treatment sessions, and after a while no further progress will be made. Thus, if the control device 140 monitors progress of the user and finds that progress has slowed down or has even come to a standstill, the control device 140 may conclude that the user is an experienced user and may set the tolerance margins accordingly. However, this again requires the use of a memory to log the user's performance.

Further, the mere fact that a user has used the device many times is no guarantee that this user will actually perform well.

It is therefore preferred that the control device 140 analyses the sensor output signal $S_V$, and rates the user's skills on the basis of the outcome of this analysis, in real time. A suitable feature of the sensor output signal $S_V$ is the stability, and a suitable parameter for assessing the speed stability is a frequency profile, which can be determined by real time Fourier transformation, for instance. In a simplified embodiment, the amplitude of the sensor output signal $S_V$ at a certain frequency or within a certain frequency band or above a certain cut-off frequency may be used. Particularly, a larger high-frequency content present in the measured data would correspond to lower stability.

The analysis of the sensor output signal and the adaptation of the tolerance margins can be done within a few seconds, i.e. during actual use, so that the control device 140 at all times adapts the device to the skills of the actual user virtually instantaneously. It is preferred that the control device 140 stores the values of the tolerance margins in the memory 141, so that a "run-in" time can be reduced the next time that the device is used again. Further, in the out-of-the-box state of the device, the margins can be set at maximum.

Increasing the tolerance margins inevitably involves accepting the fact that the device is not operated in optimum conditions. In order to reduce the risk of possible harm to the user's skin, in a possible embodiment the control device 140 reduces the power of the treatment action performer 110 in conjunction with an increase of the tolerance margins.

Figure 8:
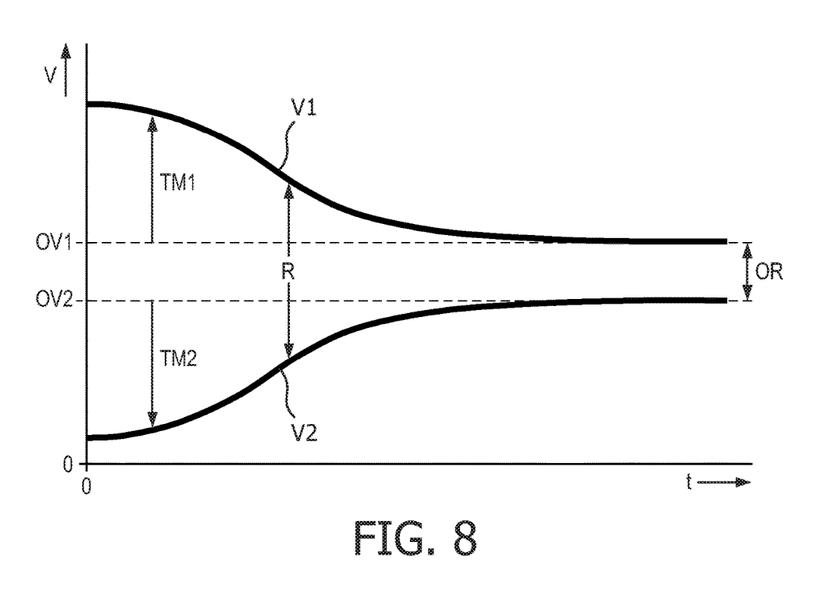
FIG. 8 is a graph illustrating the amendment of speed threshold tolerance margins over time.

FIG. 8 is a graph, comparable to FIG. 4, illustrating approximately the effect of the present invention in practice. Initially, at t=0, the upper and lower thresholds V1 and V2 are relatively far apart, with the tolerance margins TM1 and TM2 being at their maximum. The tolerated speed range R is relatively wide. With time, the width of the tolerated speed range R is reduced: the tolerance margins TM1 and TM2 are reduced and the upper and lower thresholds V1 and V2 move towards each other, until eventually they coincide with the operational upper and lower limits OV1 and OV2, respectively. For sake of convenience, the figure shows a steady development, while in reality the changes will only occur while the device is in actual use, as should be clear. Further, the changes may be step-wise.

It is noted that in practice it may happen that the control device 140 finds the speed stability to be reduced as compared to a previous time, so that the control device 140 increases the tolerance margins TM1 and TM2 again. This may for instance happen if the user has not used the device for some time, or if a less-skilled user uses the device after a skilled user.

Summarizing, the present invention provides a skin treatment device with adaptive motion feedback to assist the user in learning to use the device with a constant displacement speed without correcting an inexperienced user too often. Briefly stated, a skin treatment device according to the present invention comprises:
  a housing;
  a treatment action performer arranged within the housing for performing a treatment action on the user's skin;
  a speed sensor for sensing a relative speed between the housing and the user's skin;
  a speed feedback signalling device;
  a control device receiving an output signal from the speed sensor.

The control device actuates the speed feedback signalling device if the output signal received from the speed sensor is outside a tolerated displacement speed range. The tolerated displacement speed range is adapted to the performance skills of the user regarding moving the device with a constant speed. If the user has low skills, the control device widens the tolerated displacement speed range. If, over time, the user gets more experience and hence the performance skills become better, the control device will narrow down the tolerated displacement speed range.

While the invention has been illustrated and described in detail in the drawings and foregoing description, it should be clear to a person skilled in the art that such illustration and description are to be considered illustrative or exemplary and not restrictive. The invention is not limited to the disclosed embodiments; rather, several variations and modifications are possible within the protective scope of the invention as defined in the appended claims. For instance, the device may be part of an apparatus that further comprises a base station, for instance a docking station with a battery charger or a station with an optical light source.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. Even if certain features are recited in different dependent claims, the present invention also relates to an embodiment comprising all of these features. Any reference signs in the claims should not be construed as limiting the scope.

In the above, the present invention has been explained with reference to block diagrams, which illustrate functional blocks of the device according to the present invention. It is to be understood that one or more of these functional blocks may be implemented in hardware, where the function of such a functional block is performed by individual hardware components, but it is also possible that one or more of these functional blocks are implemented in software, so that the function of such a functional block is performed by one or more program lines of a computer program or a programmable device such as a microprocessor, microcontroller, digital signal processor, etc.

The invention claimed is:

1. Skin treatment device comprising:
a housing whose shape and size are suitable for being held by a human hand;
a treatment action performer associated with the housing for performing a treatment action on a user's skin;
a speed sensor for sensing a relative displacement speed (V) between the housing and the user's skin in a device displacement direction (X) parallel to a surface of the skin;
a speed feedback signalling device comprising a signal generator for generating a signal perceivable by a human; and
a control device provided with an associated memory containing information defining a tolerated displacement speed range (R) having an upper threshold (V1) and a lower threshold (V2),
wherein the control device is coupled to receive an output signal ($S_V$) from the speed sensor and is coupled to provide a control signal to the speed feedback signalling device,
wherein the control device is adapted to compare the speed sensor output signal ($S_V$) with said upper threshold (V1) and with said lower threshold (V2), and to control the speed feedback signalling device such as to generate a first feedback signal when the speed sensor output signal ($S_V$) indicates that the relative displacement speed (V) is higher than said upper threshold (V1) and to generate a second feedback signal when the speed sensor output signal ($S_V$) indicates that the relative displacement speed (V) is lower than said lower threshold (V2),
wherein the control device is further adapted to monitor a parameter indicative of a degree of a user's ability to move the skin treatment device at a correct speed,
wherein the control device is further adapted to set a relatively large magnitude of, or increase the magnitude of, the tolerated displacement speed range (R) if said parameter indicates a relatively low degree of said user's ability, and
wherein the control device is further adapted to set a relatively small magnitude of, or decrease the magnitude of, the tolerated displacement speed range (R) if said parameter indicates a relatively high degree of said user's ability.

2. Skin treatment device according to claim 1,
wherein the skin treatment device has a target operational range (OR) of the relative displacement speed (V), the target operational range having a target operational upper limit (OV1) and a target operational lower limit (OV2);
wherein the control device is further adapted to calculate the upper threshold (V1) according to the formula V1=OV1+TM1 and to calculate the lower threshold (V2) according to the formula V2=OV2−TM2, in which:
V1 indicates the value of the upper threshold,
V2 indicates the value of the lower threshold,
OV1 indicates the value of the target operational upper limit,
OV2 indicates the value of the target operational lower limit,
TM1 indicates an upper tolerance margin, and
TM2 indicates a lower tolerance margin; and
wherein the control device is further adapted to increase at least one of said upper and lower tolerance margins (TM1, TM2) for users with a relatively low degree of said user's ability, and to decrease at least one of said upper and lower tolerance margins (TM1, TM2) for users with a relatively high degree of said user's ability.

3. Skin treatment device according to claim 1, wherein the first feedback signal and the second feedback signal are mutually different.

4. Skin treatment device according to claim 1, wherein the control device is adapted to analyse the speed sensor output signal ($S_V$) and to rate the parameter indicative of the degree of said user's ability in real time on the basis of the outcome of this analysis.

5. Skin treatment device according to claim 4, wherein the control device is adapted to analyse the speed sensor output signal ($S_V$) by obtaining and analysing a frequency profile of the speed sensor output signal.

6. Skin treatment device according to claim 4, wherein the control device is adapted to analyse the speed sensor output signal ($S_V$) by measuring and analysing an amplitude of the speed sensor output signal at a certain frequency or within a certain frequency band or above a certain cut-off frequency.

7. Skin treatment device according to claim 1, wherein the control device is adapted to monitor a number of times and/or an amount of time that the device has actually been used, and to decrease the magnitude of the tolerated displacement speed range (R) as the number of times that the device has actually been used increases and/or the amount of time the device has actually been used increases, respectively.

8. Skin treatment device according to claim 1, wherein the control device is adapted to store, in the memory, data defining the magnitude of the tolerated displacement speed range (R).

9. Skin treatment device according to claim 2, wherein the control device is adapted to store, in the memory, data defining the values of the upper and lower tolerance margins (TM1, TM2).

10. Skin treatment device according to claim 2, wherein the control device is adapted to store, in the memory, data defining the target operational range (OR).

11. Skin treatment device according to claim 10, wherein the control device is adapted to adapt the target operational range (OR).

12. Skin treatment device according to claim 11, further comprising a skin-type sensor for determining a skin type of the user's skin, and wherein the control device is adapted to adapt the target operational range (OR) to the skin type determined by the skin-type sensor.

13. Skin treatment device according to claim 1, wherein the control device is adapted to adapt a power level of the treatment action performer in conjunction with an adaptation of the magnitude of the tolerated displacement speed range (R), wherein an increase of the magnitude of the tolerated displacement speed range (R) is associated with a reduction of the power level.

14. Skin treatment apparatus comprising the skin treatment device according to claim 1.

* * * * *